United States Patent [19]
Montgomery, IV

[11] Patent Number: 4,851,020
[45] Date of Patent: Jul. 25, 1989

[54] ETHANE RECOVERY SYSTEM

[75] Inventor: George J. Montgomery, IV, Houston, Tex.

[73] Assignee: McDermott International, Inc., New Orleans, La.

[21] Appl. No.: 274,243

[22] Filed: Nov. 21, 1989

[51] Int. Cl.⁴ .................................................. F25J 3/02
[52] U.S. Cl. ........................................... 62/24; 62/48.1
[58] Field of Search ...................................... 62/24, 54

[56] References Cited

U.S. PATENT DOCUMENTS

| | | | |
|---|---|---|---|
| 3,000,188 | 9/1961 | Greco | 62/54 |
| 3,420,068 | 1/1969 | Petit | 62/54 |
| 4,171,964 | 10/1979 | Campbell et al. | 62/24 |
| 4,278,457 | 7/1981 | Campbell et al. | 62/24 |
| 4,318,723 | 3/1982 | Holmes et al. | 62/20 |
| 4,350,511 | 9/1982 | Holmes et al. | 62/17 |
| 4,453,958 | 6/1984 | Gulsby et al. | 62/28 |
| 4,464,190 | 8/1984 | Gulsby et al. | 62/24 |
| 4,687,499 | 8/1987 | Aghili | 62/24 |

Primary Examiner—Ronald C. Capossela
Attorney, Agent, or Firm—Robert J. Edwards; Michael L. Hoelter

[57] ABSTRACT

A method of recycling a portion of the overhead vapor stream to enhance ethane recovery from a demethanizer. After the overhead vapor stream is discharged from the demethanizer, a portion of it, reflux, is compressed in a cyrogenic compressor to a pressure greater than that of the demethanizer. Afterwards the pressurized reflux is chilled in a heat exchanger causing at least a portion of it, and preferably all of it, to condense to a liquid. The pressure of this condensed reflux is then equalized to that of the demethanizer across a recycle valve so that a liquid reflux can be fed back to the top of the demethanizer. This recycling of a liquid reflux enhances ethane recovery as a column bottoms product from the demethanizer.

4 Claims, 2 Drawing Sheets

ETHANE RECOVERY SYSTEM

FIELD OF THE INVENTION

This invention pertains to a method of separating hydrocarbon gas constituents and more particularly to a method for the increased recovery of ethane.

BACKGROUND OF THE INVENTION

The process of separating hydrocarbon gas constituents is well known in the art. If the process utilizes a demethanizer then methane and other more volatile components are separated from the ethane and less volatile components of the gas stream. Should, however, the process utilize a de-ethanizer, then ethane and more volatile components (including methane) are separated from propane and less volatile components of the stream. In either case, the "recovered" components are in the column bottoms product while the "rejected" components are in the overhead vapor stream.

Many patents relating to this technology exist with each describing a unique method or improvement. Their emphasis, however, is generally directed to the processing of the hydrocarbon gas before it enters a demethanizer, de-ethanizer of other similar structure. Seldom is there emphasis on the processing of the overhead vapor stream after it leaves the demethanizer, etc. (e.g., U.S. Pat. Nos. 4,453,958 and 4,464,190 to Gulsby). However, some of those that do process the overhead vapor stream, such as U.S. Pat. Nos. 4,171,964 and 4,278,457 to Campbell et al., simply warm this stream from the demethanizer in a heat exchanger before transporting it elsewhere.

Other patents, such as U.S. Pat. Nos. 4,318,723 and 4,350,511 to Holmes et al., not only warm this overhead vapor stream, but also condense a portion of it and return this condensed portion to the distillation column as reflux. Perhaps the most pertinent patent is U.S. Pat. No. 4,687,499 to Aghili which first warms then compresses the overhead vapor stream before returning a portion of it back to the demethanizer as reflux, but only after this reflux portion has first been chilled and expanded.

While all of these processes are functional, only Holmes et al. and Aghili recycle a portion of the removed vapor stream back to the column as a liquid. Holmes et al. condenses a portion of the vapor stream while Aghili's expansion of the chilled overhead vapor product causes some of this gas to condense into a liquid. The return of a liquid reflux is desirable because it is the condensed liquid that increases the recovery percentage of the desired column bottoms product. Analysis has shown that the reflux effect is optimized when the vapor recycle stream is totally condensed before expansion to the demethanizer operating pressure. Subcooling of the condensed reflux stream is usually less effective than increasing the rate of non-subcooled condensed liquid. Unfortunately, however, a large portion of the reflux streams of Holmes et al. and Aghili are still vapor which does not increase product recovery. Instead, this uncondensed vapor mixes with the residue gas in the demethanizer and both are summarily discharged as the overhead vapor stream.

It is thus an object of this invention to provide a process whereby a recycle stream containing liquid is returned to the top of a demethanizer for increased ethane recovery in the column bottoms product. An additional object of this invention is to provide a recycle stream that is totally condensed thereby maximizing the recovery of ethane. A further object is to reduce the size of the recycle stream equipment and hardware yet provide the same amount of liquid reflux to the top of the demethanizer as is currently accomplished by Aghili or Holmes et al. Another object, should the same size equipment be used for this process as is used for conventional processes, it to deliver more liquid reflux to the top of the demethanizer column. Still another object of this invention is to reduce the number of expander-compressors and other equipment needed since the recycle stream is fully condensed. These and other objects of this invention will become apparent upon a further reading of this application.

SUMMARY OF THE INVENTION

In accordance with this invention, an overhead vapor stream is removed from the top of a demethanizer. A portion of this stream is separated from the main overhead vapor stream with this separated reflux stream being compressed to a pressure greater than that of the demethanizer. This reflux is then chilled or cooled in a heat exchanger thereby causing at least a portion of it but generally all of it to condense to liquid. The pressure of this chilled and at least partially liquid stream is then equalized to that of the demethanizer so that it can be fed or recycles back to the top of the demethanizer. The effect of this liquid (as compared to a vapor) in the demethanizer increases its operational efficiency and enhances the recovery of ethane from the demethanizer as a column bottoms product.

DETAILED DESCRIPTION OF THE DRAWINGS

Figure 1:
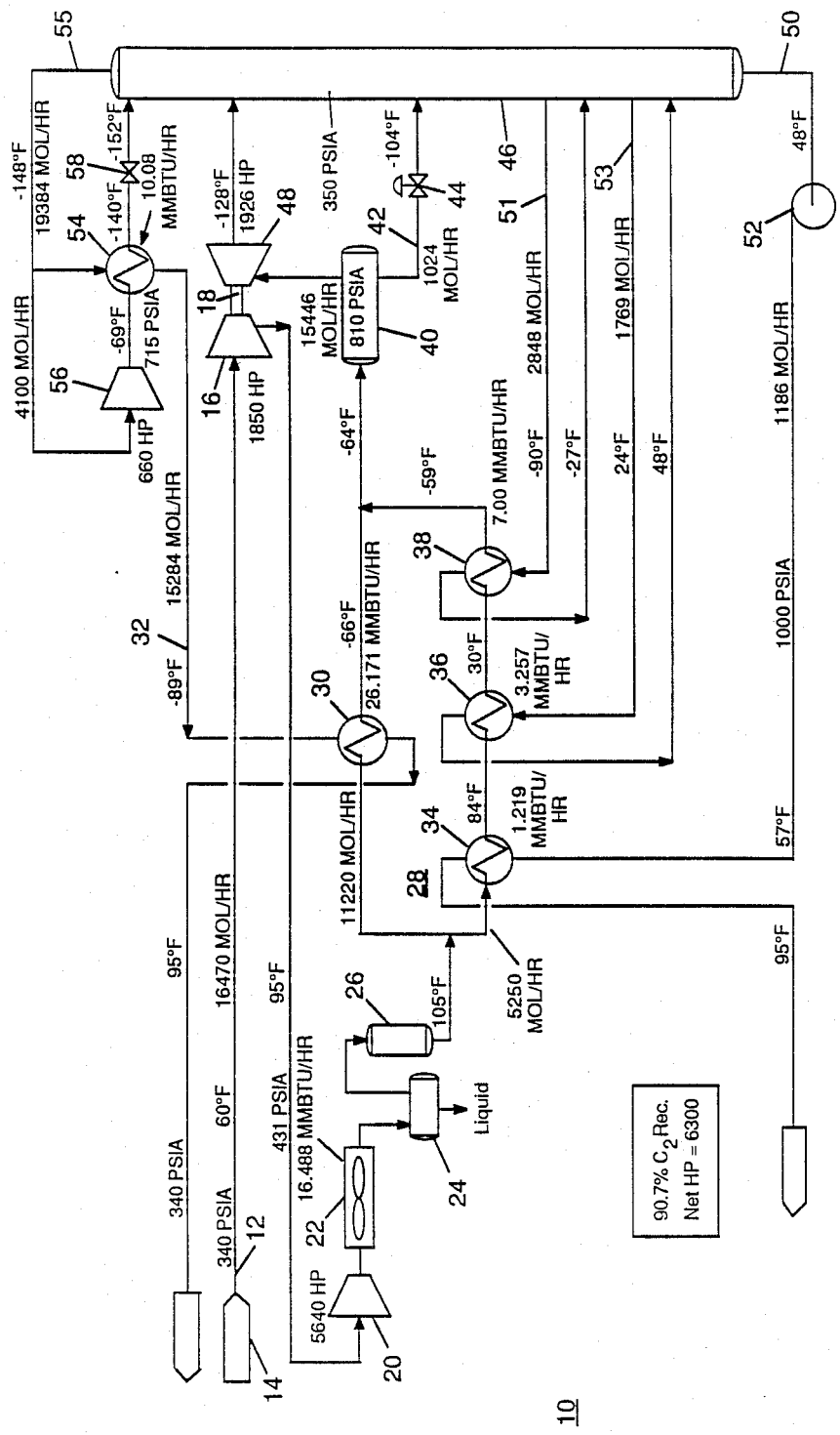
FIG. 1 is a schematic illustration of the various components of this invention showing in particular how a portion of the overhead vapor stream from the demethanizer is recycled back to the top of the demethanizer.
Figure 2:
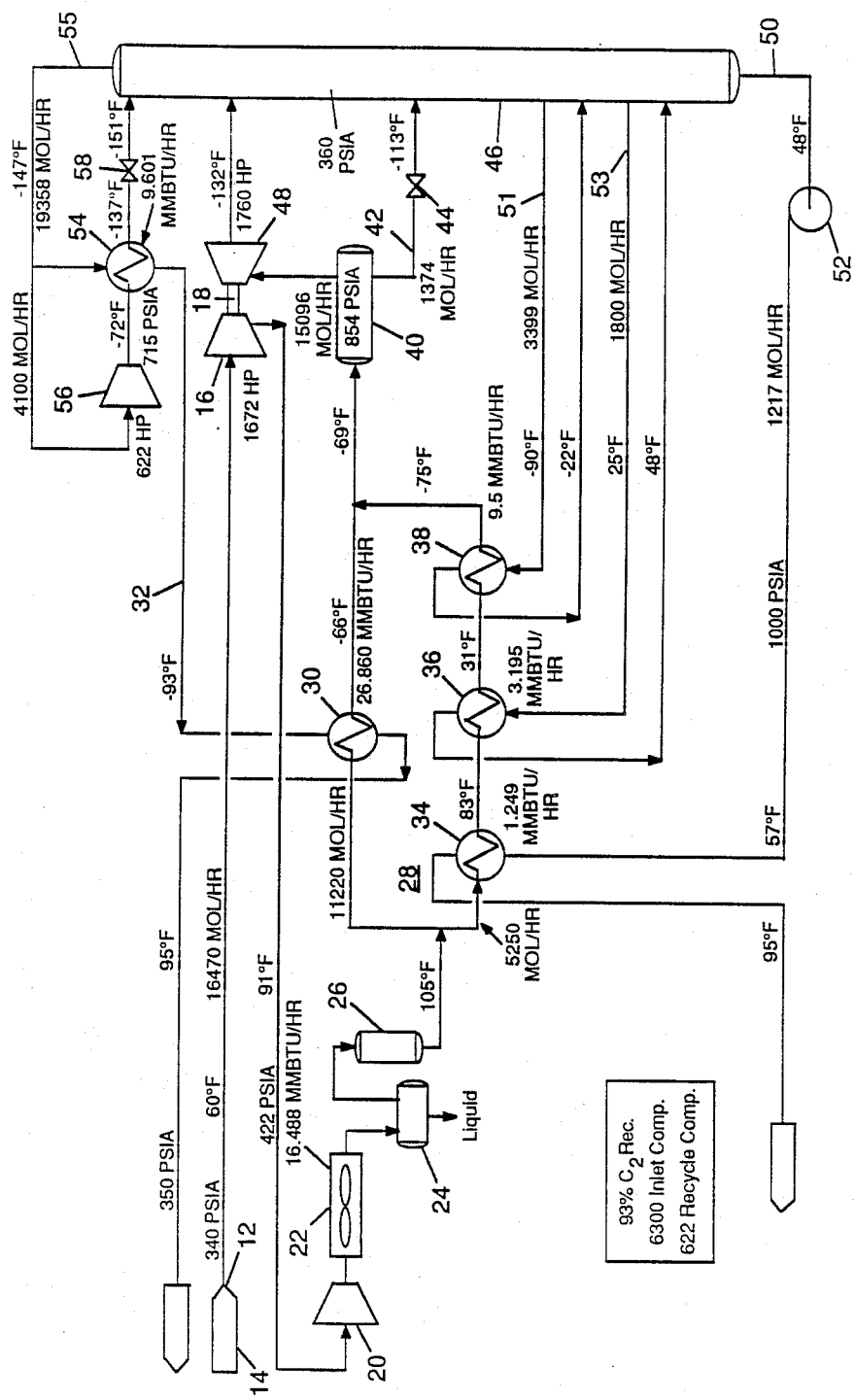
FIG. 2 is a schematic illustration similar to FIG. 1 yet showing the process parameters resulting from an approximate 10% increase in the overall horsepower requirements along with a slight increase in the operating pressure of the demethanizer.

Referring to the drawings, there is shown a schematic illustration of ethane recovery process 10. Various values of temperature and pressure are recited througout this illustration, but it should be emphasized that these are approximate values only and are recited solely as an aid in describing process 10. There should be no mistaking these approximate values as the only values applicable. To illustrate this, FIG. 2 is the same process as that shown in FIG. 1 except that the cryogenic compressor and inlet compressor are operating at different horsepower ratings. This change alone causes many different values of pressure and temperature to occur. With this understanding of the following pressure and temperature values being descriptive of only one of many variations of process 10, the intricacies of this process can be more fully described and understood.

A cleaned, filtered, and in all likelihood, dehydrated natural gas stream 12 enters ethane recovery process 10 thorugh inlet 14. In this embodiment and at this stage, natural gas stream 12 will be supplied inlet 14 at the temperature of approximately 60° F. and at a pressure of about 340 psia. In this example, the molar flowrate of stream 12 is taken to be 16470 MOL/HR (pound-mole/hour). Stream 12 flows into compressor end 16 of expander-compressor 18 where its pressure is increased to about 431 psia and its temperature is raised to around 95° F. The anticipated horsepower rating of compressor end 16 is approximately 1850 H.P. Gas stream 12 is then further compressed in inlet gas compressor 20 driven by a gas turbine or other prime mover. In accordance with FIG. 1, inlet gas compressor 20 is operating at a horsepower rating of approximately 5640 H.P.

This highly pressurized gas stream is then cooled by cross exchange with air, water, or any other process by inlet gas compressor discharge cooler 22. The rating of compressor discharge cooler 22 for this example is 16.488 MMBTU/HR (million BTU per hour). Afterwards, high pressure gas stream 12 is sent to separator 24 where any liquid whihc may have formed in the previous compression or cooling steps is removed. The gas stream from separator 24 is then dehydrated in dessicant bed driers or in any other suitable gas dehydrator 26. At this point, the temperature of the dehydrated natural gas is about 105° F. which is subsequently cooled in inlet heat exchange train 28.

Cooling of gas stream 12 is accomplished in inlet heat exchange train 28 by splitting the stream and sending the major portion (approximately 11220 MOL/HR) to gas-gas exchanger 30 where it is cooled by cross exchange with demethanizer overhead vapor stream 32. The rate of cooling of gas-gas exchanger 30 is around 26.171 MMBTU/HR. After such cooling, this portion of stream 12 is chilled to a temperature of about minus 66° F. The remainder of gas stream 12 (about 5250 MOL/HR) is delivered, in series, to demethanizer bottoms heater 34, demethanizer reboiler 36, and demethanizer side reboiler 38 heat exchangers. Each of these heat exchangers operate at different cooling levels with demethanizer bottoms heater 34 operating at approximately 1.219 MMBTU/HR, demethanizer reboiler 36 operating at approximately 3.257 MMBTU/HR, and demethanizer side reboiler 38 operating at approximately 7.00 MMBTU/HR. After the first cross exchange in bottoms heater 34, the temperature of this portion of gas stream 12 is about 84° F., after reboiler 36, the temperature is approximately 30° F. and after side reboiler 38, the temperature is about minus 59° F. Upon combining the previously separated streams, the temperature of the mixture settles around minus 64° F. It should be noted that additional refrigeration of the gas stream may occur either while it is separated or after being combined, as needed.

The combined cooled inlet stream then flows to cold separator 40 which generally is at a pressure of about 810 psia. Here, any condensed liquid is separated from the uncondensed gas stream. Line 42 transfers this condensed liquid (having a flow rate of about 1024 MOL/HR) across cold separator liquid valve 44 and to a lower feed tray of demethanizer 46. At this lower feed inlet, liquid stream 42 has a temperature of about minus 104° F. and its pressure, which has been reduced via valve 44, is approximately that of the demethanizer, here operating at approximately 350 psia.

Vapor from cold separator 40 (having a flow rate of approximately 15446 MOL/HR) flows through expander end 48 of expander-compressor 18 where its pressure is reduced from the 810 psia found in cold separator 40 to that of demethanizer 46 (approximately 350 psia). The horsepower rating of expander end 48 is approximately 1926 H.P. and expander-compressor 18 lowers the temperature of this vapor stream to about minus 128° F. before it is fed to a middle feed location of demethanizer 46.

Within demethanizer 46, methane and lighter, more volatile constituents of natural gas stream 12 vaporize and separate from such heavier counterparts as ethane, propane, butane, etc. Ethane and these heavier constituents are recovered as demethanizer column bottoms product and are removed from demethanizer 48 via line 50. Before being recovered, the ethane is warmed to a temperature of about 48° F. after being crossexchanged with the inlet natural gas stream in reboiler 36 and side reboiler 38 heat exchangers. As shown in FIG. 1, line 51 transmits a portion of the flow (approximately 2848 MOL/HR) in demethanizer 46 to and from side reboiler heat exchanger 38. This flow is initially at a temperature of about minus 90° F. before it is cross exchanged with gas stream 12 at a temperature of about 30° F. After such exchange, gas stream 12 is chilled to about minus 59° F. while line 51 is warmed to about minus 27° F.

Likewise, line 53 transmits about 1769 MOL/HR from demethanizer 46 for cross exchange in reboiler heat exchange 36. Prior to such heat exchange, line 53 is at a temperature of about 24° F. whereas after such heat exchange in reboiler 36, its temperature rises to approximately 48° F. At the same time the cross exchanging fluid, stream 12, has its temperature reduced from approximately 84° F. to about 30° F.

As indicated earlier, demethanizer bottoms product departs demethanizer 46 via line 50 at a temperature of about 48° F. Upon departure, demethanizer pump 52 pressurizes this ethane and other heavier components to a pressure of about 1000 psia causing its temperature to increase to about 57° F. After such pressurization, this liquid, having a flow rate of about 1186 MOL/HR, flows through bottoms heater 34 where it is cross exchanged with gas stream 12. In bottoms heater 34, the demethanizer bottoms product has its temperature raised from approximately 57° F. to about 95° F. whereas gas stream 12 is chilled from approximately 105° F. to about 84° F. Afterwards, the ethane and other heavier consituents of the natural gas stream are transported elsewhere for further processing.

The lighter overhead methane gas stream exits the top of demethanizer 46 via line 55 at a temperature of about minus 148° F. This overhead vapor stream is split into two streams, the majority (approximately 15284 MOL/HR) flows first through recycle exchanger 54 and then through gas-gas exchanger 30 before being transported elsewhere. Recycle exchanger 54 raises the temperature of this majority portion of the line 55 from approximately minus 148° F. to about minus 89° F. while gas-gas exchanger 30, which is in cross exchange with incoming gas stream 12, raises its temperature to approximately 95° F. At this temperature, and at a pressure of about 340 psia, the majority of the overhead vapor stream (i.e., the lighter methane and other more volatile components) are transported elsewhere for further processing.

A smaller portion of this overhead methane gas stream or reflux (approximately 4100 MOL/HR) is directed to cyrogenic compressor 56. This compressor 56, which is rated at about 660 HP, increases the pressure of this minority portion of line 55 from approximately 350 psia (the pressure of demethanizer 46) to about 715 psia. In doing so, the temperature of this reflux stream is raised from approximately minus 148° F. to about minus 69° F. This compressed methane gas reflux is then condensed by cross-exchange with the majority of the overhead methane gas stream in recycle exchanger 54. The capacity of recycle exchanger 54 is about 10.08 MMBTU/HR and such cross-exchange lowers the temprature of the reflux to about minus 140° F. The compressed reflux leaving recycle exchanger 54 may be partially condensed, totally condensed, or totally condensed and subcooled in exchanger 54 depending on the parameters chosen by the operator. The parameters described herein will provide a totally condensed stream. No matter its state, this reflux stream passes through recycle valve 58 which reduces its pressure to that of demethanizer 46 (i.e., approximately 350 psia) while also lowering its temperature to about minus 152° F. This compressed, cooled, and condensed reflux, which initially formed a portion of overhead methane gas stream 55, is then recycled back to the top of demethanizer 46 where the condensed liquid increases the efficiency and ability of demethanizer 46 to separate methane from the other natural gas components thereby producing more ethane as a column bottoms product.

Referring now more specifically to FIG. 2, the same process is followed with the differences being an approximate 10% increase in the overall horsepower requirement of ethane recovery process 10 and a change in the operating pressure of demethanizer 46. The horsepower supplied to cryogenic compressor 56 in FIG. 2 is actually reduced about 10% from the process shown in FIG. 1 (from approximately 660 HP in FIG. 1 to about 622 HP in FIG. 2). Furthermore, the horsepower supplied inlet gas compressor 20 is increased about 10% over that disclosed in FIG. 1 (from approximately 5640 HP to about 6300 HP). With these changes, the pressure in cold separator 40 is raised from approximately 810 psia to about 854 psia. Also, the pressure in demethanizer 46 is raised from approximately 350 psia to about 360 psia. These changes have the specific effect of altering certain pressure and temperature values of process 10 with the overall effect being to increase the efficiency of ethane recovery from about 90.7% (FIG. 1) to about 93% (FIG. 2).

In natural gas streams containing carbon dioxide, the proposed process achieves higher levels of ethane recovery than a conventional process. This is because for a given ethane recovery percentage, the proposed process allows the demethanizer to operate at a temperature and pressure higher than that of a conventional process. Such higher operating temperature and pressure places the system operating conditions further away from the conditions under which solid carbon dioxide forms. Now, if the operating conditions of the proposed process are moved closer to the solid carbon dioxide formation conditions, ethane recovery will increase even more and, likewise, operating horsepower will increase. Depending on the carbon dioxide content of a particular feed gas stream, the horsepower requirements, if desired, may be increased up to the level of the conventional process, or the operating conditions may maintain a critical distance from solid carbon dioxide formation conditions. Nevertheless, all in all, the ethane recovery will be higher and the operating horsepower will be lower than for a conventional process.

Another feature of ethane recovery process 10 is that recycle stream which is totally condensed can be supplied demethanizer 46 to maximize ethane recovery. This can be accomplished by proper control of the interrelationship between cyrogenic compression 56, recycle exchanger 54, recycle valve 58 and the operating pressure of demethanizer 46. Consequently, should a user desire a certain amount of liquid reflux, the above equipment can be installed for just that amount so that oversized or undersized equipment can be avoided. Additionally, due to the fact that the reflux is all liquid, a reflux expander-compressor is not necessary. The power recovery and cooling obtained from a liquid expander is not significant enough to be economical. Simply reducing the condensed reflux stream's pressure across a valve adequately satisfies the process requirements.

Finally, the decoupling or separation of the above recycle/reflux scheme from the inlet supply process makes each process separately controllable. It is a disadvantage to have these schemes overlap because in doing so it becomes very difficult, if not impossible, to operate process 10 should something be wrong with the reflux system. By decoupling them, the reflux system can be by-passed, if need be, without affecting inlet gas stream 12 of the operation of process 10 in the conventional manner.

In view of the above embodiment, it sould be noted that more compression activity takes place on the inlet side of demethanizer 46 as contrasted with the discharge or residue gas side of demethanizer 46. One basic variation which is not shown in the drawings is to reverse this and shift the main compression duty from the inlet gas stream to the residue gas stream. This variation is needed when inlet natural gas stream 12 is available at a high pressure and overhead vapor stream 32 (the residue gas stream) must also be delivered at a high pressure. To accomplish this, compressor 16 of expander-compressor 18 would be relocated in above process 10 so as to compress residue gas stream 32 after it is warmed in gas-gas exchanger 30. The warmed gas leaving expander-compressor 18 would normally then be further compressed by a residue gas compressor which is driven by an electric motor, gas engine, turbine, or other prime mover. Such high pressure gas would then be cooled by cross exchange with air, water, or any other available process or utility stream. This cooled, high pressure gas is then delivered as the residue gas product stream.

What is claimed is:

1. A method of improving ethane recovery from natural gas wherein condensed liquid is returned to a demethanizer as reflux comprising the steps of:
   (a) removing overhead vapor from a demethanizer,
   (b) compressing a portion of said overhead vapor, now reflux, to a pressure greater than that of said demethanizer,
   (c) reducing the temperature of said compressed relux thereby causing at least a portion of it to condense, the temperature of said compressed reflux being reduced by cross-exchanging it with an uncompressed portion of said overhead vapor in a heat exchanger;
   (d) equalizing the pressure of said reflux to that of said demethanizer; and
   (e) feeding said reflux back to said demethanizer.

2. The method as set forth in claim 1 wherein said reflux is totally condensed before being fed to said demethanizer.

3. The method as set forth in claim 2 wherein said reflux is compressed in a cyrogenic compressor.

4. The method as set forth in claim 3 wherein the pressure of said reflux is equalized to that of said demethanizer across a recycle valve.

* * * * *